US007405653B2

(12) United States Patent
Tice et al.

(10) Patent No.: US 7,405,653 B2
(45) Date of Patent: Jul. 29, 2008

(54) SYSTEM FOR MONITORING ACTIVITIES AND LOCATION

(75) Inventors: Lee D. Tice, Bartlett, IL (US); Robert J. Clow, North Aurora, IL (US); Dragan P. Petrovic, Geneva, IL (US)

(73) Assignee: Honeywell International Inc., Morristown, NJ (US)

( * ) Notice: Subject to any disclaimer, the term of this patent is extended or adjusted under 35 U.S.C. 154(b) by 159 days.

(21) Appl. No.: 11/150,946

(22) Filed: Jun. 13, 2005

(65) Prior Publication Data

US 2007/0008111 A1 Jan. 11, 2007

(51) Int. Cl.

| | |
|---|---|
| ***G08B 1/08*** | (2006.01) |
| ***G08B 23/00*** | (2006.01) |
| ***A61B 5/00*** | (2006.01) |
| *H04Q 7/00* | (2006.01) |

(52) U.S. Cl. .............................. 340/539.12; 340/573.1; 340/522; 340/521; 340/506; 600/300; 128/904

(58) Field of Classification Search ............ 340/539.12, 340/522, 521, 506

See application file for complete search history.

(56) References Cited

U.S. PATENT DOCUMENTS

| | | | | |
|---|---|---|---|---|
| 5,564,429 | A | 10/1996 | Bornn et al. | 128/696 |
| 5,752,976 | A * | 5/1998 | Duffin et al. | 607/32 |
| 5,794,219 | A | 8/1998 | Brown | 705/37 |
| 5,822,715 | A | 10/1998 | Worthington et al. | |
| 5,828,943 | A | 10/1998 | Brown | |
| 5,832,448 | A | 11/1998 | Brown | |
| 5,879,163 | A | 3/1999 | Brown | |
| 5,897,493 | A | 4/1999 | Brown | |
| 5,899,855 | A | 5/1999 | Brown | |
| 5,913,310 | A | 6/1999 | Brown | |
| 5,918,603 | A | 7/1999 | Brown | |
| 5,933,136 | A | 8/1999 | Brown | |
| 5,940,801 | A | 8/1999 | Brown | |
| 5,951,300 | A | 9/1999 | Brown | |
| 5,959,529 | A * | 9/1999 | Kail, IV | 340/539.12 |
| 5,960,403 | A | 9/1999 | Brown | |
| 5,985,559 | A | 11/1999 | Brown | |
| 5,997,476 | A | 12/1999 | Brown | |
| 6,002,994 | A * | 12/1999 | Lane et al. | 702/188 |
| 6,032,119 | A | 2/2000 | Brown et al. | |
| 6,050,940 | A | 4/2000 | Braun et al. | 600/300 |
| 6,101,478 | A | 8/2000 | Brown | |
| 6,144,837 | A | 11/2000 | Quy | |
| 6,151,586 | A | 11/2000 | Brown | |
| 6,161,095 | A | 12/2000 | Brown | |
| 6,167,362 | A | 12/2000 | Brown et al. | |
| 6,168,563 | B1 | 1/2001 | Brown | |
| 6,186,145 | B1 | 2/2001 | Brown | |

(Continued)

OTHER PUBLICATIONS

U.S. Appl. No. 10/956,681, filed Oct. 1, 2004, Kiff et al.

(Continued)

*Primary Examiner*—Donnie L Crosland
(74) *Attorney, Agent, or Firm*—Welsh & Katz, Ltd.

(57) ABSTRACT

A residential monitoring system incorporates both physiological sensors and activity sensors. Some of the sensors can be in wireless communication with control circuitry. One or more activity profiles can be established for a resident to expand upon and supplement information from the physiological sensors.

11 Claims, 2 Drawing Sheets

U.S. PATENT DOCUMENTS

| | | | | |
|---|---|---|---|---|
| 6,210,272 | B1 | 4/2001 | Brown | |
| 6,233,539 | B1 | 5/2001 | Brown | |
| 6,246,992 | B1 | 6/2001 | Brown | |
| 6,248,065 | B1 | 6/2001 | Brown | |
| 6,260,022 | B1 | 7/2001 | Brown | |
| 6,270,455 | B1 | 8/2001 | Brown | |
| 6,334,778 | B1 | 1/2002 | Brown | |
| 6,368,273 | B1 | 4/2002 | Brown | |
| 6,375,469 | B1 | 4/2002 | Brown | |
| 6,381,577 | B1 | 4/2002 | Brown | |
| 6,389,301 | B1 | 5/2002 | Furuya | |
| 6,402,691 | B1 | 6/2002 | Peddicord et al. | |
| 6,612,984 | B1 | 9/2003 | Kerr, II | |
| 6,705,990 | B1 | 3/2004 | Gallant et al. | |
| 6,723,046 | B2 | 4/2004 | Lichtenstein et al. | 600/300 |
| 6,825,761 | B2 * | 11/2004 | Christ et al. | 340/506 |
| 2005/0242946 | A1 * | 11/2005 | Hubbard et al. | 340/539.12 |
| 2006/0033625 | A1 * | 2/2006 | Johnson et al. | 340/573.1 |
| 2006/0055543 | A1 * | 3/2006 | Ganesh et al. | 340/573.1 |

OTHER PUBLICATIONS

PCT International Search Report from corresponding PCT application, published May 16, 2007.

PCT Int'l Preliminary Report on Patentability corresponding to PCT/US2006/022471 mailed Jan. 3, 2008.

PCT Written Opinion of the International Searching Authority corresponding to PCT/US2006/022471 mailed Jan. 3, 2008.

* cited by examiner

SYSTEM FOR MONITORING ACTIVITIES AND LOCATION

FIELD OF THE INVENTION

The invention pertains to residential monitoring systems. More particularly, the invention pertains to systems that sense and/or evaluate activity information relative to at least one resident.

BACKGROUND OF THE INVENTION

Known in-home monitoring systems at times combine scheduled sensing of physiological parameters of a resident with an exchange of information to a remote location. At that remote location, a monitoring person, or agent, may assist the resident through messages. Many of the known systems only measure predetermined physiological parameters of the resident. This is only a partial indication of an individual's health.

A resident may not realize when his/her behaviors are contributing to a potential decrease in health. Furthermore, many health related issues of the individual may not be included in the query that the individual answers. Thus the resident's health may be degrading without it being detected by the remote monitor. In addition, even if an abnormality is detected, it may be difficult to determine the reason—even if a nurse is called to visit the resident later.

There is thus a continuing need to be able to better assess the health of individuals whose activities of daily living may be impacted by one physiological condition or another. Preferably, much functionality would be compatible with and integratable into an upgraded in-residence monitoring system. It would be further desirable to be able to create and maintain an activity profile. Such a profile could exist as an averaged activity representation of an individual's activities. Alternatively, it could exist as a plurality of different daily activities.

Further, it would be desirable to take into account the comings and goings of a resident. In known systems where a displaced monitor can make calls to check on the condition or status of an individual, a failure to answer can be a cause for concern. Thus, it would be preferable to be able to advise the displaced monitor as to the presence or absence of the respective individual from the residence.

DETAILED DESCRIPTION

Figure 1:
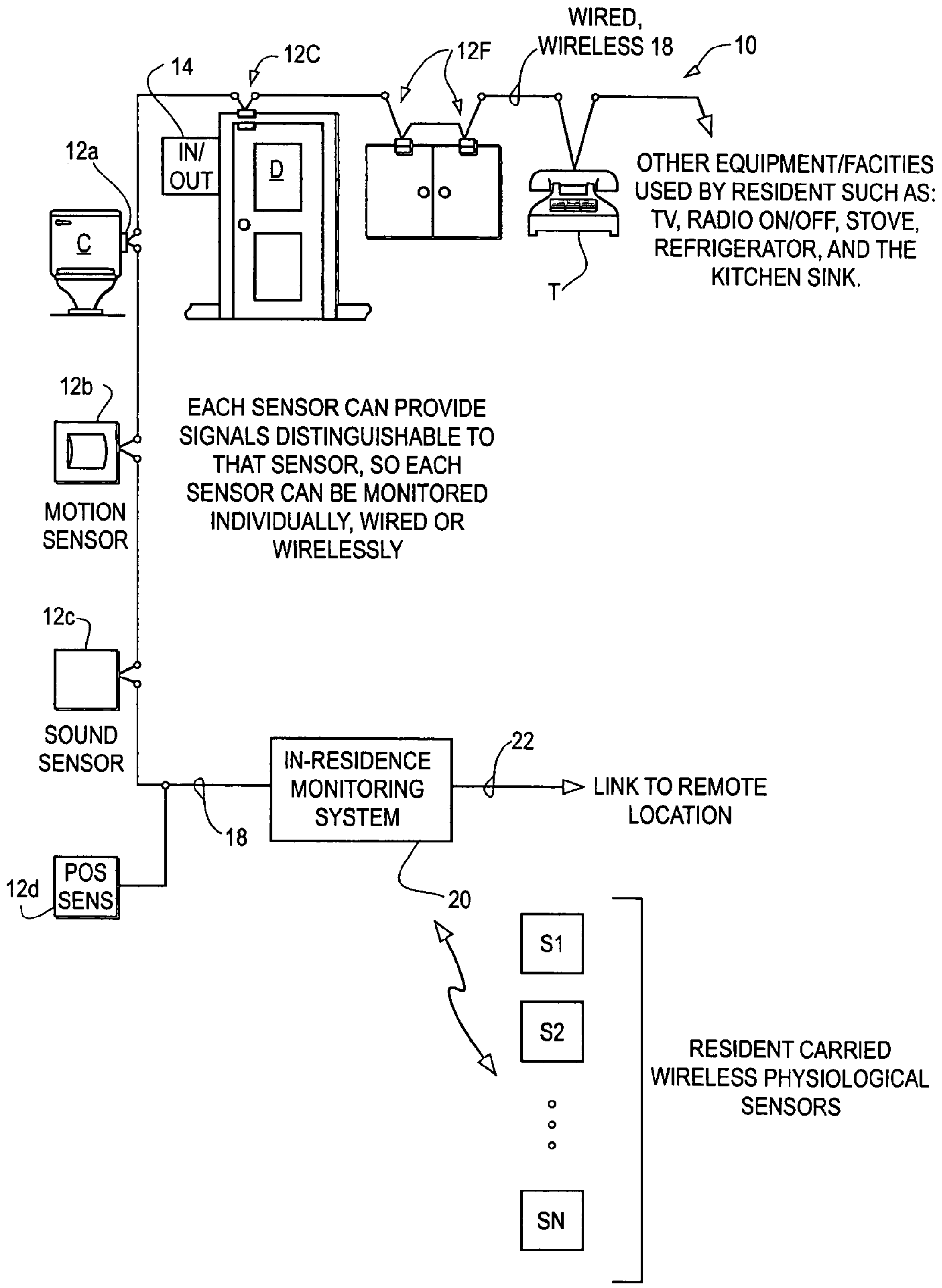
FIG. 1 is a block diagram of a system in accordance with the invention.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

Embodiments of this invention overcome a deficiency known of types of systems that rely upon the resident to provide the information accurately indicating his/her condition and success in the following of plans. The activities of the resident can be monitored to see if they are consistent, or "normal". What is established as "normal" can be based upon the prior healthy activity history of that person. It can also be customized for the residence. The advantage of this system is that a health care professional visiting to provide care can be aware of the activities of the resident and can use that information to assess the health status of the resident.

Some of these normal activities can include the use of bathroom facilities, use of kitchen facilities, entertainment equipment, or movement from one location to another.

A variety of in-residence activities can be sensed to determine if a person is healthy and/or in need of a call or visit and associated care.

Possible activities that can be sensed include:

1. A resident's daily use of bathroom facilities and significant deviations therefrom that may indicate a health related problem. The bathroom facility monitoring can also include sensors that indicate whether the person is standing by or sitting on a commode and for what durations. Additional sensors can provide more information about the situation.

2. A resident's use of water sources in the residence may be indicative of a potential hydration problem for the person. Flow sensors or other types of sensors can be included to monitor water consumption. Sensors can take into account the use of bottled water or water sources not attached to plumbing.

3. A resident's use of the kitchen facilities can be sensed relative to proper consumption of food and their particular consumption pattern(s). This can include monitoring the stove, refrigerator, microwave, garbage container, and storage compartments/drawers.

4. A resident's use of the entertainment equipment on a normal basis. This can include monitoring the changing of channels on the TV, using a radio, etc.

5. A resident's exercising is part of a normal routine. The exercise patterns or equipment can be monitored for amount of use and duration.

6. A resident's time spent in one room in a chair can be monitored. Motion sensors or position sensors can track movement.

7. A resident's use of the cleaning, washing, or other facilities indicative of good hygiene can be monitored.

8. A resident's communications patterns including use of the telephone or other outside communication devices can be intermittently or continuously evaluated.

When a resident significantly deviates from normally expected activities within predetermined time periods, then a system in accordance with the invention could initiate a communication with the resident to encourage activity. Such action by the resident could be as simple as responding to the system.

If a communication exchange or response activity does not occur, a monitor or automatic call could be placed to the residence to check on the resident's condition. This call could also be incorporated into the query call that may be scheduled at predetermined times. This call could query the resident on concerns over their activities and enable the resident to respond prior to scheduling a personal visit.

Many factors can lead to inactivity including pain and depression. A person in a depressive state may answer a telephone query as being OK. However, lack of activities would cause concern and may provide a more accurate indicator to systems that embody the present invention.

Measurement devices can include acoustical sensors, contact sensors, motion sensors, position sensors, water flow sensors, all without limitation.

Acoustical sensors can detect sounds of activity in a kitchen or bathroom. Each activity can be expected to have a unique sound pattern that the system recognizes. For example, the amplitude/frequency sounds of water running, voices (with and without stress) or television, drawers opening/closing, doors opening/closing, toilets flushing, exercise equipment operating and the like can be sensed, without limitation. If a medication dispenser is equipped to emit a predetermined sound pattern when opened/closed, the medication taking activity could also be monitored.

Motion sensors could be located throughout the residence. They not only provide information as the movement of the resident but they also give indications that more than one person is in the residence. If motion is detected in the bedroom and kitchen simultaneously, then it can be determined that at least two occupants are in the residence. That can provide information to caregivers or others on an automatic calling list that are remotely monitoring the resident and indicate a problem if only one person is expected to be in the residence. Likewise, if motion is detected at 3 a.m. and several other times during the night, it may indicate the resident is experiencing a problem.

Sensors may be carried by the resident to indicate physiological condition as well as position, such as whether he/she is lying down or standing or sitting. This can be accomplished using at least one position sensor. If a person is lying down in an area of the residence that does not contain a bed or sofa to accommodate lying down, then a problem may have been detected. If the resident remains in a lying down position for longer than an expected time, then it may also indicate a problem with the mobility and associated activity of that resident.

In an other aspect of this invention, a global positioning system (GPS) monitor could be carried by the resident for exercising or activity outside the residence. The GPS can monitor movement and location. If a resident has a problem with memory and finding their way to the residence, then they can be tracked and located. If the resident is leaving the approved perimeter of a residence, an alarm can be sounded.

Activity information can be accumulated in a central unit in the residence, analyzed, and a report forwarded to a remote location relative to the activity of the resident for any period of time, day and night.

The in-home system can also be equipped with an input that the resident can activate when leaving the home so the monitoring system doesn't go into an alert due to a failure of the resident to respond to an automatic query at a scheduled time that day. This provides freedom for the resident to schedule other necessary events that may have him/her out of the home at the pre-scheduled query call time.

The monitoring system can incorporate a push-button switch or other device that the resident can activate when leaving the home so system status is "out-of-home". When an automatic query is initiated by a monitoring station or other part of the system, a message can be sent to the central station that the resident is "out-of-home" and to retry at a later time without generating alerts or follow up calls. In addition, the "out-of-home" setting can automatically active an "out-of-home" message for phone calls incoming to the home.

When the resident returns, the resident re-activates the system as "in-home" or the system automatically recognizes their return (sensors in home) and switches the system back to "in-home" operation. At that time, the monitoring station can reinitiate the query that was missed by the resident being out of home.

If the time the resident is going "out-of-home" is very close to the prescribed medication or query time, then the system could request that the resident perform the monitored function(s) prior to leaving. If the home is equipped with monitors that can identify that the patent has left the home, then that monitor could hold a system alert until a later time.

If the resident is leaving the home, the person could input an estimated time of return and the system will reschedule the query/alert until after the estimated return time.

In another aspect, a central unit or computer could use voice recognition to converse with the resident prior to leaving such that the system resets the time of a query. If the resident will be visiting a relative or vacationing, then the "out-of-home" setting may include new location information that the query cold be re-routed to. In some cases, the query could be conducted by a monitoring person if the monitoring equipment is not available at the new location. It may further incorporate date/time information that the new location will become active incorporating travel time. Likewise, the new location may be used to provide information as to when the "in-home" setting will become active upon a return to home.

If there is significant variation of actual return to "in-home" from "out-of-home" programmed times, a call be generated to relatives or other authorized persons to notify them of this variation. The resident could alter the estimated time of return to "in-home" when "out-of-home" by using a phone, which can include a cell phone, and a personal code.

A log of "in-home" and "out-of-home" dates/times can be maintained in either the local system or the central monitoring system If the system is set by the resident as "out-of-home" but sensors detect the resident as "in-home", the system can instruct the resident to reset the system to the correct setting or automatically reset the system. If authorized persons are in the home, a cleaning service or maid for example, while the resident is absent, alternate methods can be used to disregard or overcome the outputs of sensors as previously described.

FIG. 1 illustrates a system 10 in accordance with the present invention. System 10 can be incorporated into a residential facility or a residence having one or more rooms or the like used by a resident.

The system 10 provides a plurality of sensors which are associated various facilities within the residential area. For example and without limitation, system 10 can incorporate a vibration or flow sensor **12*a*** which could be associated with a commode C for sensing flushing thereof.

One or more motion sensors **12*b* can be located throughout the residential area to provide feedback as to movement of the resident in the area. One or more sound sensors 12*c*** could be located throughout the residential area which could respond to both verbal and non-verbal audio indicia indicative of a resident's condition.

System 10 can also incorporate one or more position sensors **12*d*** which could provide position information relative to the resident. At least one such sensor could be carried by the resident.

Additional sensors could include one or more door sensors **12*e* which could indicate opening or closure of a respective door D. Additionally sensors 12*f*** could be mounted on a plurality of cabinet doors to provide feedback as to when the residence is accessing the respective cabinets. The cabinets could store medications, groceries, clothing, towels, bedding or the like all without limitation. Other sensors without limitation could be installed and used to sense whether other equipment or facilities routinely use by the resident such as entertainment (television, radio or the like), stove, refrigerator or kitchen sinks is being used and if so when.

Additionally, a present/absent or in/out indicator can be provided by a manually operable unit 14. The unit 14 can be located adjacent to the door D and can include a button lever or the like which is triggered or operated by the resident as he or she goes in or out through the door D.

The unit 14 provides feedback to the system 10 that the resident has left the area. A subsequent signal can be generated upon the return of the resident to the area.

Sensors 12, unit 14 as well as other sensors and communication devices, such as telephone T can be in wired or wireless communication via a medium 18 with a local monitoring system 20. It will be understood that the details of the monitoring system 20 are not a limitation of the present invention.

Each of the sensors associated with the system 10 such as 12, 14, telephone T as well as sensors associated with other equipment or facilities of the residents can provide feedback via the medium 18 to the monitoring system 20 which are indicative of the activities of the resident. Such activity can be accumulated by the system 20 and analyzed to provide feedback and/or information via wired or wireless link 22 to one or more remote locations. The remote locations can be associated with relatives, neighbors, friends as well as a staffed monitoring station. The system 20 can be in wired or wireless communication with a plurality of physiological sensors S1 . . . Sn which can be worn or carried by the resident during daily activities.

Processing by the system 20 can provide feedback via the link 22 as to ongoing daily activities being undertaken by the resident. A variation from expected normal activity levels can cause a prompt to be communicated by a link 22 to system 20, or can cause the system 20 to generate a prompt via link 22 to one or more remote locations relative to the deviation from normal expected activity.

Figure 2:
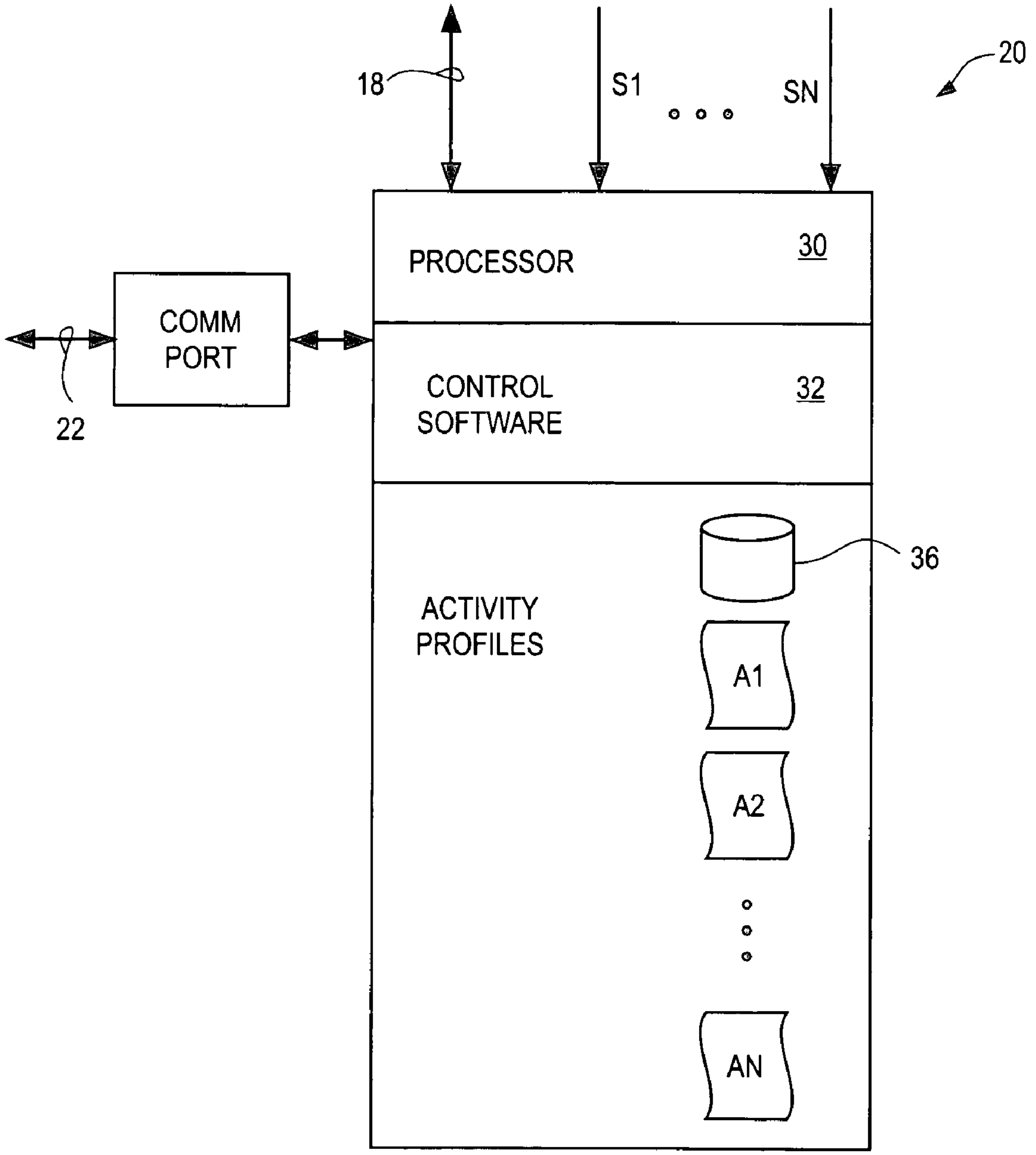
FIG. 2 is a block diagram of additional details of the system of FIG. 1

FIG. 2 illustrates in block diagram form an exemplary embodiment of the system 20. System 20 can incorporate a programmable processor 30 and associated control software 32. The software in combination with the processor 30 can respond to signals from the various sensors 12, 14, telephone T, S1 . . . Sn as well as other types of sensors to create a plurality of activity profiles A1, A2 . . . An indicative of expected or "normal" activity of the resident. Such profiles can be retained in a memory, disk drive or optical memory 36 in a data base which can be searched and analyzed.

The subject data base can be analyzed on a daily basis and respective activity levels can be compared to average expected activity levels based on multiple day averages for example to establish whether the resident is fuctioning at his or her normal levels. Similarly, feedback from the various physiological sensors S1 . . . Sn can also be incorporated into the respective profiles A1, A2 . . . An and provide real time information as to selected physiological conditions of the resident.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A system comprising:

at least one sensor of a physiological condition of an individual;

at least one sensor of activity of the individual;

control circuitry local to and wired to at least some sensors, the control circuitry evaluates sensor activity of the individual as well as at least one sensed physiological condition of the individual and, responsive thereto, determines the presence of an abnormal condition;

software executed by the control circuitry to establish a plurality of locally stored activity profiles indicative of expected activities of the individual; and additional software to compare sensed current activities to at least one profile, and responsive thereto, to communicate with the individual wherein the activity profiles are created from multiple day averages of activity levels of the individual.

2. A system as in claim 1 wherein the control circuitry includes a communications port, the port provides at least unidirectional communications between the control circuitry and a displaced device.

3. A system as in claim 2 including circuitry to transmit information relating to at least sensed activities from the communications port.

4. A system in claim 3 where the control circuitry includes software to evaluate the sensed physiological condition of the individual.

5. A system as in claim 3 where the control circuitry includes software to evaluate the sensed activities of the individual.

6. A system as in claim 3 which includes a manually operable indicator of absence of the individual.

7. A system in claim 6 which includes software to evaluate the presence or absence of an individual from a region.

8. A system as in claim 1 which includes a plurality of activity sensors.

9. A system as in claim 8 where members of the plurality are selected from a class that includes at least acoustic sensors, fluid flow sensors, motion sensors, position sensors, communications sensors, orientation sensors, exercise equipment usage sensors, and at least one sensor of presence/absence of an individual from a region.

10. A system as in claim 8 where the control circuitry includes at least one of a personal computer or a residential monitoring apparatus.

11. A system comprising:

at least one sensor of a physiological condition of an individual;

at least one sensor of activity of the individual;

control circuitry local to and wired to at least some sensors, the control circuitry evaluates sensor activity of the individual as well as at least one sensed physiological condition of the individual and, responsive thereto, determines the presence of an abnormal condition, the control circuitry includes a communications port, the port provides at least unidirectional communications between the control circuitry and the displaced device, the control circuitry transmits information relating to at least sensed activities from the communications port;

software executed by the control circuitry to establish a plurality of locally stored activity profiles indicative of expected activities of the individual;

additional software to compare sensed current activities to at least one profile, and responsive thereto, to communicate with the individual wherein the activity profiles are created from multiple day averages of activity levels of the individual; and software to evaluate the presence or absence of an individual from a region.

* * * * *